United States Patent [19]

Orth et al.

[11] 4,157,311
[45] Jun. 5, 1979

[54] METHOD OF MAKING A HALOGEN SENSOR

[75] Inventors: Edward D. Orth, Boxford; William J. Schultz, Lynnfield, both of Mass.

[73] Assignee: General Electric Company, New York, N.Y.

[21] Appl. No.: 829,899

[22] Filed: Sep. 1, 1977

[51] Int. Cl.$^2$ .................. C01N 27/62; C09K 3/00; H01J 7/24
[52] U.S. Cl. .................. 252/408; 23/232 R; 23/232 E; 422/90; 73/19; 73/23; 106/73.4; 252/518; 264/60; 264/61; 264/66; 324/33; 315/111
[58] Field of Search ............ 23/232 R, 232 E, 254 E, 23/255 E; 73/19, 23; 252/408, 518; 106/73.4; 264/60, 61, 66; 315/111; 324/33

[56] References Cited

U.S. PATENT DOCUMENTS

| | | | |
|---|---|---|---|
| 3,471,746 | 10/1969 | Roberts | 315/111 |
| 3,895,963 | 7/1975 | McCowan | 106/73.4 |
| 3,979,625 | 9/1976 | Roberts | 73/23 |
| 3,991,360 | 11/1976 | Orth et al. | 73/19 |
| 4,013,477 | 3/1977 | Jatkar et al. | 106/73.4 |
| 4,082,826 | 4/1978 | Iijima | 106/73.4 |

OTHER PUBLICATIONS

Ray, A. K., et al., Mat. Res. Bull., vol. 10, No. 6, pp. 583-590 (1975).
"Comprehensive Inorganic Chemistry," vol. 1, Bailar, Jr., et al., editors, Pergamon Press, N.Y., p. 1036 (1973).

Primary Examiner—Padgett, Benjamin R.
Assistant Examiner—T. S. Gron
Attorney, Agent, or Firm—R. G. Simkins

[57] ABSTRACT

A method of making a mixture of sensing material for a halogen vapor sensor characterized by providing granular activated Alumina ($Al_2O_3$) and firing it in a sensitizing material, in the class of alkali metals including carbonates of sodium, lithium, potassium, cesium and rubidium, under controlled temperature conditions for a predetermined time to distribute the sensitizing metal throughout the interstices of the Alumina.

4 Claims, 3 Drawing Figures

METHOD OF MAKING A HALOGEN SENSOR

BACKGROUND OF THE INVENTION

The invention relates to a method for manufacturing a mixture of sensing material and more particularly to a method for making a mixture of sensing material having improved ion efficient characteristics for a given volume of material heated to a predetermined temperature to provide enhanced indicating instrument sensitivity when the sensing mixture is assembled in an electrical gas detection device and exposed to a flow of halogen vapor.

It is well known to use electrical gas detection devices to detect ions collected at oppositely charged emitter and collector electrodes near which a mixture of ion emitting material is positioned. Typically, such a sensing device includes a cylindrical negative electrode having a helically wound positive heater electrode coaxially disposed around it. The negative electrode is formed of a relatively inert material such as platinum and is filled with a mixture of sensing material such as granules of ceramic coated with an alkali metal. In using a device of this type to detect gas leaks; for example, leaks in refrigeration systems or other systems of piping in which a halogen tracer gas has been introduced, it is only necessary to draw a sample of gas from adjacent the system, through a suitable tubular probe, into contact with the sensor element of the indicating device. As the sample gas is passed through or near the heated electrodes, sensing material located within the negative electrode induces a flow of ions from the alkali source mixture at a rate that varies dependent on the concentration of halogen gas in the sample gas.

Examples of such prior art vapor detectors are disclosed in U.S. Pat. No. 2,795,716-Roberts and U.S. Pat. No. 3,439,262-Roberts, both of which are assigned to the assignee of the present invention. As explained in yet another patent, U.S. Pat. No. 3,471,746-Roberts, also assigned to the same assignee, one operating difficulty encountered with the use of electrical discharge vapor detecting devices is that they are highly sensitive to variations in temperature of the mixture of sensing material. Thus, it is desirable to either provide a constant heat input to the sensing material, based upon empirical heat loss data for a given sensing element, or to provide an accurate temperature control for the sensor in order to assure accurate and reliable indications of current rate between the emitter and collector of the instrument. The need to control the heater temperature of such an instrument is complicated by the fact that the heat developed by the heating coil varies as the square of the voltage applied to it and the sensitivity of the sensing mixture increases logarithmically with respect to temperature variations.

Practical engineering considerations such as limitations on size and economic constraints on design costs make it particularly difficult to provide the desired level of accuracy in vapor detecting instruments when the instruments must be made small enough to be conveniently portable. On the other hand, the large number of leak detecting applications in which it is desirable to have a portable gas detecting instrument make it very desirable to overcome these difficulties. Thus, it would be particularly useful to provide a halogen detecting instrument that incorporates an alkali metal sensing mixture in which a relatively small volume of sensing material affords a sufficiently large and uniform current flow to provide an accurate indication of a detected halogen vapor when the mixture of sensing material is heated to a given temperature. Moreover, it would be advantageous to provide a method of making such a sensing mixture that enables the mixture to be heated to its most ion efficient state by a heater that requires a relatively low level of energizing power.

Accordingly, it is an object of the present invention to provide a method for making a sensing mixture for a halogen gas sensor instrument that is capable of producing a relatively large indicating current from a small volume of sensing material that can be readily heated to an optimum emission temperature by a small heater current.

Another object of the invention is to provide a method of making a mixture of sensing material for a halogen gas detector in which an unusually large area of alkali metal is dispersed throughout the interstices of a small volume of supporting granular material.

Yet another object of the invention is to provide a method of manufacturing a mixture of sensing material for a halogen gas sensor such that the heat sensing mixture is economically produced and affords reliable and efficient ion emission characteristics.

Additional objects and advantages of the invention will be apparent to those skilled in the art from the description of it that follows considered in conjunction with the accompanying drawing.

SUMMARY OF THE INVENTION

In one preferred sequence of the method of the invention, a batch of granular activated Alumina ($Al_2O_3$) is baked in an inert metal crucible to completely dry the Alumina. A metal alkali such as rubidium carbonate or other suitable sensitizing material is then mixed in a predetermined ratio with the Alumina, stirred to expose the Alumina granules to the carbonate material, and baked under controlled conditions to diffuse the sensitizing material throughout the interstices of the Alumina. The activated Alumina and its large surface to volume ratio, combined with judicious quantities of alkali dopant, keep hygroscopicity of the dopant under control so that unacceptable amounts of moisture do not accumulate in the sensor during periods when the heater is turned off and adversely effect the device by causing electrode shorting. Suitable activated Alumina is available in a variety of grain sizes, so an appropriate size for a given application can be readily selected. After a final baking operation the sensing mixture is stored in a vapor-tight container until it is to be assembled in the sensing element of a halogen gas detector instrument.

DESCRIPTION OF THE PREFERRED EMBODIMENT

Figure 3:
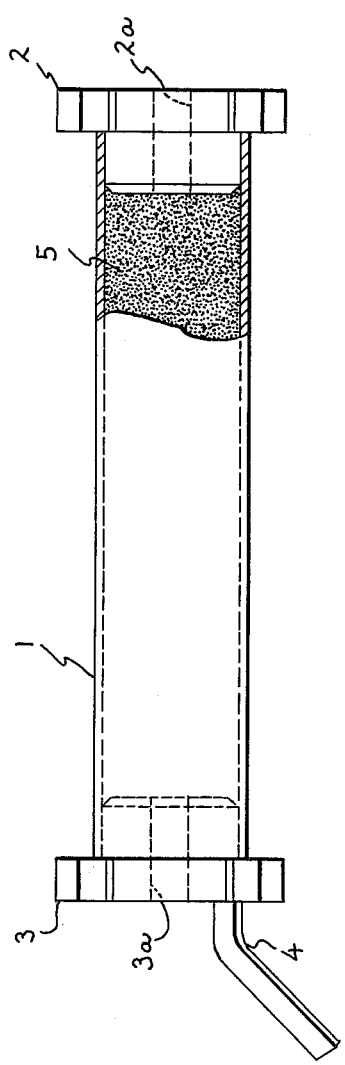
FIG. 3 is a side elevation of a tube assembly for housing a sensing mixture made according to the method of the invention so that the mixture may be mounted in operating relationship within a conventional halogen gas detector instrument.

It should be understood from the discussion of the background of the invention presented above that the method of the invention can be used to manufacture a variety of different kinds of sensing elements for halogen vapor detectors. A basic type of sensing element for a halogen vapor detector is shown in one of the above mentioned patents, namely, U.S. Pat. No. 3,439,262, which illustrates a sensor formed of alkali metal glass with rubidium packed in a platinum coated negative electrode element. One problem encountered with such detectors in the past is that the large silica content compound used develops whiskers across the gap between the elements of the sensor; thus, it is apparent that a substantially lower silica contact in the sensing mixture is needed to prevent the formation of such undesirable whiskers. A sensing assembly somewhat similar to that shown in this patent is illustrated in FIG. 3 of the drawing herein for the purpose of orienting the description of the method of the present invention. However, the platinum tube 1 is filled with granular activated Alumina 5 that is prepared according to the method of the present invention in order to obtain the objects of the invention set forth above and to provide a mixture that does not develop whiskers in the electrode gap of the sensor.

Thus, referring to FIG. 3 it will be seen that there is shown a platinum tube 1 having ceramic end caps 2 and 3 which, respectively, are provided with axial apertures 2A and 3A therethrough. An electrical conductor 4 is connected to the platinum tube 1, in the manner more fully described in U.S. Pat. No. 3,439,262 with reference to the analogous elements 12 and 14 illustrated in FIG. 3 of that patent. Although a heater coil is not illustrated in FIG. 3, those skilled in the art will recognize that when the sensing element is assembled in operating position in a halogen detecting instrument a conventional coil will be disposed in spaced relation around the sensing element.

It will be understood that this sensing element can be used in a halogen vapor detector such as that shown in the patent referenced immediately above, or a mixture of sensing material prepared according to the invention may be formed in alternative desired configuration. For example, there is shown in relatively recently issued U.S. Pat. No. 3,991,360 a generally cylindrically shaped halogen sensing element that is formed by such a method and further characterized by fusing the treated granular Alumina into a tubular element and tightly wrapping it with a heater coil to construct the invention disclosed and claimed therein.

Figure 1:
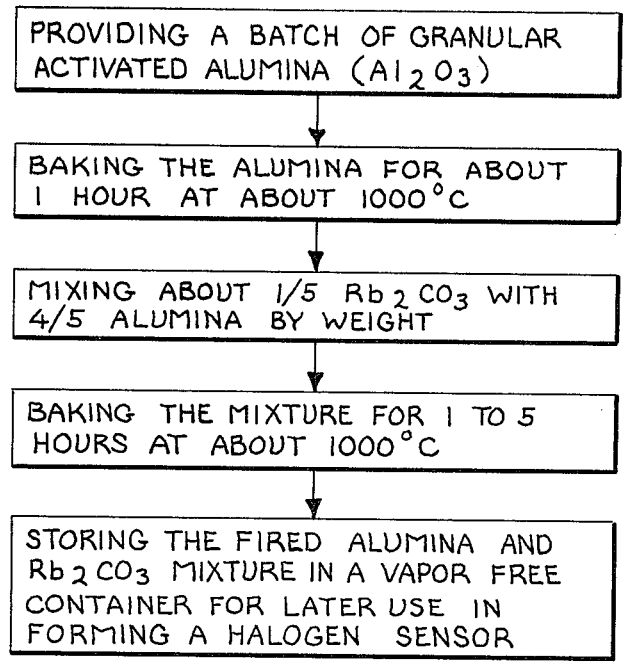
FIG. 1 is a flow chart of one preferred sequence of the method of the invention.

Now, bearing in mind the types of sensing devices that may be made from granular mixtures of sensing material manufactured by the method of the invention, reference is made to FIG. 1 of the drawing which lists a preferred series of method steps for practicing the invention. Thus, it will be seen that according to the method of the invention one first provides a batch of granular activated Alumina ($Al_2O_3$). We have found that commercially available activated Alumina granules sold under the tradename Alcoa Type F-1 is suitable for use in the method of the invention. The granules of this type of activated Alumina are sufficiently porous to provide an unusually large surface area on which alkali metal is subsequently deposited. Also, the granules of Alumina are rugged enough to prevent their being broken down into fine powder, if properly handled, during the mixing and firing operations of the method that will be discussed below.

According to the method of the invention the granular Alumina is placed in an inert metal crucible, such as a platinum crucible, and is baked for about 1 hour at approximately 1,000° C. Following this baking step of the invention the crucible and its contents are cooled to an ambient temperature and either stored in a vapor-tight container for future use or immediately further processed pursuant to the method of the invention. In the latter case the next method step of the invention involves placing a powder taken from the class including carbonates of sodium, lithium, potassium, cesium or rubidium in the Alumina-containing platinum crucible in an amount equal in weight to about one-fourth the weight of the Alumina in the crucible. In the preferred sequence of the method of the invention depicted in FIG. 1, rubidium carbonate powder is used in practicing this step of the invention.

At this point in the manufacturing sequence, alternative procedures may be followed. In order to assure a suitable intermixing of the Alumina and the powdered alkali metal, pursuant to one alternative sequence of the invention, the contents of the crucible are covered with acetone and stirred sufficiently to completely expose the Alumina granules to the rubidium carbonate, taking care not to reduce the size of the Alumina granules by the stirring operation. According to an alternative sequence of the method of the invention, it has been found possible to eliminate the use of the acetone bath and simply to stir the Alumina and powdered alkali metal together to completely intermix them prior to the following basic steps.

After the contents of the crucible are completely intermixed by either of the foregoing procedures, the mixture is placed in a suitable oven and baked about 1 hour at approximately 1,000° C. in order to completely diffuse the alkali metal through the interstices of the Alumina granules. After this second baking operation the crucible and its contents are cooled to the ambient temperature and the fired Alumina and rubidium carbonate mixture is stored in a vapor-tight container for subsequent use in forming a sensing element such as that shown in FIG. 3 of the drawing.

From the foregoing description of the preferred sequence of the method of the invention it will be apparent that various alternative sequences may be used in practicing the invention without departing from its true spirit and scope. Thus, in alternative applications of the invention any of the other alkali metal carbonates noted above may be substituted instead of the rubidium carbonate. Also, it has been found that if the second baking cycle, i.e., the baking cycle in which the alkali metal powder is fired into the Alumina granules is increased between 1 and 5 hours in duration at approximately 1,000° C., adequate dispersion of the alkali metal through the interstices of the Alumina can be reliably attained without requiring any mechanical intermixing of the powdered alkali metal and the Alumina prior to the baking operation. Moreover, although approximately 20% by weight of the alkali metal powder is used relative to the Alumina in the preferred method steps of the invention stated above, it has been found that the weight ratios may vary with the selected alkali metal ranging in weight from $\frac{1}{3}$rd to $\frac{1}{2}$ the weight of the granular Alumina without seriously adversely affecting the sensitivity of the resultant mixture of halogen sensing material, as long as humidity effects remain in control.

Figure 2:
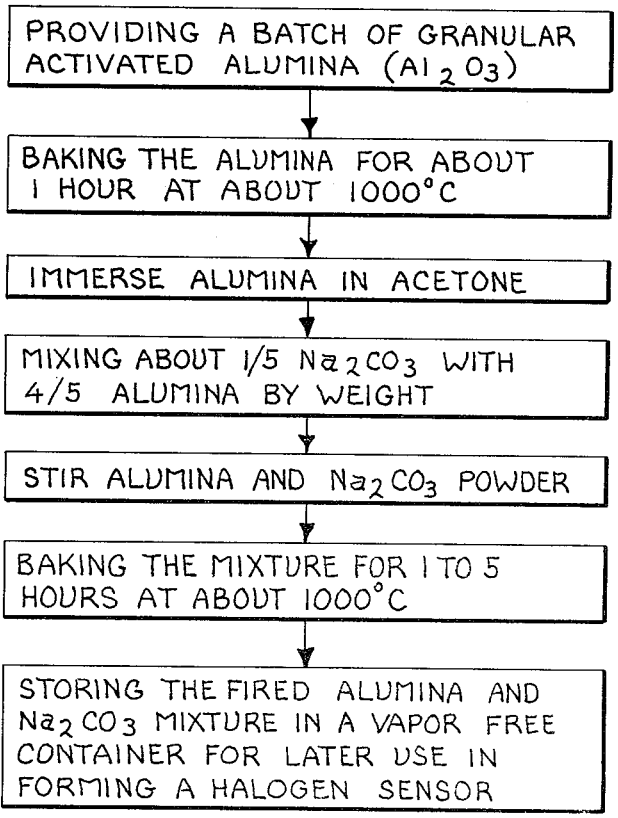
FIG. 2 is a flow chart of the steps of an alternate arrangement of the method of the invention.

Some of these alternative steps are illustrated in FIG. 2 of the drawing which is a flow chart of the method of the invention wherein sodium carbonate is used as the alkali metal powder, rather than rubidium carbonate and an acetone bath is used with a stirring operation to assure complete intermixing of the Alumina with the sodium carbonate powder prior to the second baking operation.

Further modifications and alternative forms of the invention will be apparent to those skilled in the art from the description of it presented herein. It is our intention to encompass within the scope of the following claims the true spirit of the invention.

What we claim and desire to secure by Letters Patent of the United States is:

1. A method of making a sensing mixture for a halogen gas sensor comprising an alkali metal carbonate dispersed throughout the interstices of granules of porous activated alumina having a large surface area, consisting essentially of the steps of:
   (a) providing a batch of granular activated Alumina ($Al_2O_3$),
   (b) placing the Alumina in a platinum crucible and baking it for about 1 hour at approximately 1,000° C., then cooling the crucible and its contents to ambient temperature,
   (c) placing at least one alkali metal carbonate powder selected from the group consisting of carbonates of sodium, lithium, potassium, cesium and rubidium in the crucible equal in weight to about 1/5th to about ½ the weight of the Alumina,
   (d) baking the crucible contents for about 1 hour to about 5 hours at a temperature in the range of 900° C. to 1,200° C. to diffuse the alkali metal carbonate throughout the interstices of the alumina, then cooling the crucible and its contents, and
   (e) storing the fired Alumina and alkali metal carbonate mixture in a vaportight container for subsequent use in forming a halogen gas sensor.

2. A method of making a sensing mixture for a halogen gas sensor comprising an alkali metal carbonate dispersed throughout the interstices of granules of porous activated alumina having a large surface area, consisting essentially of the steps of:
   (a) providing a batch of granular activated Alumina ($Al_2O_3$),
   (b) placing the Alumina in a platinum crucible and baking it for about 1 hour at approximately 1,000° C. then cooling the crucible and its contents to ambient temperature,
   (c) placing at least one alkali metal carbonate powder selected from the group consisting of sodium carbonate and rubidium carbonate in the crucible equal in weight to about ¼th the weight of the Alumina,
   (d) covering the contents of the crucible with acetone,
   (e) stirring the contents of the crucible sufficiently to expose the Alumina granules to the alkali metal carbonate, taking care not to reduce the size of the Alumina granules during the stirring operation,
   (f) baking the crucible contents for about 1 hour at approximately 1,000° C. to diffuse the alkali metal carbonate throughout the interstices of the alumina then cooling the crucible and contents, and
   (g) storing the fired Alumina and alkali metal carbonate mixture in a vapor-tight container for subsequent use in forming a halogen gas sensor.

3. A method of making a sensing mixture as described in claim 1 wherein the mixture of alkali metal carbonate powder and Alumina granules is baked for a period of about 1 to 5 hours at a temperature of approximately 1,000° C.

4. A method of making a sensing mixture as defined in claim 1 wherein the ratio of alkali metal powder to granular Alumina is about ¼th by weight of alkali metal carbonate powder with the remainder of the mixture being activated granular Alumina.

* * * * *